United States Patent [19]

Fee

[11] Patent Number: 5,294,796
[45] Date of Patent: Mar. 15, 1994

[54] REMOTE VAPOR DETECTION SYSTEM AND METHOD THEREOF

[75] Inventor: Maurice L. Fee, Anaheim, Calif.

[73] Assignee: Aerojet-General Corporation, Rancho Cordova, Calif.

[21] Appl. No.: 844,524

[22] Filed: Mar. 2, 1992

[51] Int. Cl.$^5$ .............................................. G01N 21/35
[52] U.S. Cl. ................................. 250/338.5; 250/339; 250/341
[58] Field of Search ................... 250/338.5, 340, 339, 250/341

[56] References Cited

U.S. PATENT DOCUMENTS 3,662,171 5/1972 Brengman et al. ................ 250/349

Primary Examiner—Carolyn E. Fields
Attorney, Agent, or Firm—Leonard Tachner

[57] ABSTRACT

A remote vapor detection system and method thereof which advantageously utilizes only one, low power, single fixed wavelength laser to heat the background surface behind a vapor cloud, the constituents of which are to be detected. The heated background acts as a broad band infrared source for measuring absorption characteristics of the gas or vapor constituents and thus does not rely on prior art techniques such as back scatter or fluorescence dependent measurements which inherently require greater power or suffer from reduced sensitivity. The system of the present invention comprises a source of suitable electromagnetic radiation, such as infrared wavelength laser and a spectrally responsive receiver which may be a spectrometer or radiometer having filters at selected wavelengths corresponding to absorption and non-absorption bands of the specie of gas or vapor being detected.

8 Claims, 3 Drawing Sheets

REMOTE VAPOR DETECTION SYSTEM AND METHOD THEREOF

BACKGROUND OF THE INVENTION

1. Field of the Invention

The present invention relates generally to remote detection of gases and vapors at low concentration levels and over short path lengths. The present invention relates more specifically to a remote vapor detection system and method thereof, in which a laser is used to heat the background immediately adjacent the vapor or gas to be detected. Such heating increases the infrared radiation of such background which then serves as an infrared source for measuring the absorption characteristics of gases or vapor clouds between the background and a wavelength selective receiver.

2. Prior Art

U.S. Pat. No. 4,496,839 to Bernstein et al is directed to a system and method for remote detection and identification of chemical species by laser initiated non-resonant infrared spectroscopy. A 9.4 micrometer wavelength laser is suggested for producing pulses of laser energy to heat the gas, liquid or aerosol form of a material to be detected. After the unknown mass is heated by a laser pulse, the non-resonant radiation from the heated mass is sampled immediately thereafter. The spectrum is then compared with known chemical specie spectrums to identify the chemical species. Thus, this prior art patent disclosure relies on the absorption coefficient of the gas or vapor, providing a sufficient excitation of the gas or vapor at a specific selected laser frequency. In addition, the use of a pulsed laser system and synchronized sampling of the radiation from the unknown mass requires the use of special timing circuitry.

U.S. Pat. No. 4,490,613 to Brame is directed to an infrared hydrocarbon remote sensor that utilizes a raster scan of a high intensity laser for excitation of hydrocarbon molecules and a receiver that detects re-radiated energy. This disclosure is similar to that of Bernstein, except that in this particular case, continuous or pulsed laser radiation can be used and wavelengths are selected that are more readily absorbed by the hydrocarbon molecules.

U.S. Pat. No. 4,999,498 to Hunt et al is directed to a is remote sensing gas analyzer that uses background radiation present in the area with a spectrometer to detect any gas having characteristic peaks in the infrared region. The radiation from the background passes through the unknown gas and into the analyzer by means of a window and a reflector. A beam splitter and corner reflectors provide an interferogram that is focused by parabolic reflectors for detection by a cooled detector. A single laser is used to determine the position of the scanned corner reflector, The system analyzes the gas absorption when the background is at a higher temperature than the gas. Thus this disclosure utilizes the natural background of the source and interferometer as a receiver.

U.S. Pat. No. 4,864,127 to Brame is directed to an earth surface hydrocarbon gas cloud detection by use of Landsat Data. A satellite receives thermal energy and reflected energy emanating from the earth because of solar energy. The satellite can direct a coherent beam of electromagnetic energy onto its field of view. The signals received by the satellite are sent to a receiving station. The data can reveal hydrocarbon gas presence by converting frequencies to composite wavelengths by combining different bands. The beam of energy directed from the satellite to the earth has a wavelength that is most effective for detecting the hydrocarbon gas cloud. The beam energizes the gas cloud and not the earth. Thus, this particular prior art patent disclosure is based on using natural thermal radiation of the earth and coherent satellite beam radiation to excite a hydrocarbon gas. The specific wavelengths are required for optimum absorption with selection of the wavelength of the satellite laser radiation highly dependent upon the absorption characteristics of the hydrocarbon gas to be detected.

U.S. Pat. No. 4,247,770 to Welch is directed to an aerial, mineral survey method and apparatus using a pulsed laser beam to vaporize surface material. This system's laser generates a high energy beam that vaporizes minerals to be analyzed. The minerals emit an atomic emission spectra characteristic of the material which is analyzed by a spectrometer to determine the makeup of the mineral structures. The infrared energy from the heating is not used to determine the makeup of the vapor by its absorption. Thus, Welch discloses a high power laser to vaporize the samples and means for measuring the atomic spectra of the vaporized samples.

U.S. Pat. No. 4,517,458 to Barringer discloses a system which uses laser energy to cause secondary emission or fluorescence. Unfortunately, the fluorescence cross-section is one or two orders of magnitude less than the absorption cross-section of a given species and therefore requires a much higher power laser compared to a system which relies on absorption.

There is therefore an ongoing need for a remote vapor detection system which does not require extremely high levels of excitation energy, which does not rely for performance on the absorption characteristic of the unknown vapor or gas at a specific wavelength, which does not require complex timing circuitry, which in fact does not rely upon the use of an energy source to heat the vapor or gas to create secondary is emission or fluorescence and which relies upon the use of only a single laser to detect all species within a broad wavelength region, such as 8 to 12 micrometers.

SUMMARY OF THE INVENTION

The aforementioned ongoing need is satisfied by the present invention which avoids all of the previously noted deficiencies of the prior art by relying on a single laser wavelength to heat the background behind the vapor or gas to be detected and thus increase the infrared radiation of the background. The enhanced background radiation serves as an infrared source for measuring the absorption of gases or vapor clouds between the background and a wavelength selective receiver. The wavelength selective receiver may be a spectrometer or radiometer having filters corresponding to the absorption wavelength of a gas species of interest and at least one reference filter corresponding to a spectral region where the gas species of interest has no significant absorption. Detection is made by comparing the response of the receiver in an absorption band to the response in the reference band. In special cases where the background is not changing over a period of time, an internal reference in the receiver may be used. In this special case, detection is determined by measuring the temporal change in the receiver signal at the absorption wavelengths of the gas specie of interest.

In an exemplary embodiment of the invention disclosed herein, a continuous wave or periodic continuous wave $CO_2$ laser is used, thereby avoiding any need for special timing circuitry. Because the described system is based on the absorption cross section which is larger than either the back-scatter or fluorescence cross-section, the present invention has an inherent advantage over back-scatter and fluorescence based systems. The wavelength of the laser is generally selected to not correspond to strong absorption bands of the vapor to be detected, such as a laser wavelength of 10.6 micrometers to detect vapors such as acetone, ether, methyl ethyl ketone, and freon 11. Laser energy causes the background behind the vapor or gas to rise in temperature. A heated background surface provides an enhanced background source of broad band infrared radiation which is selectively absorbed by the vapor cloud. A mirror architecture is used to coordinate laser and the spectrometer or radiometer performing the function of an infrared receiver. The broad band radiation from the background which has been selectively absorbed by the gas or vapor to be detected, is received by the infrared receiver which is wavelength selective. Detection occurs by measuring the received infrared radiation in a vapor's absorption band and comparing it to the radiation received in an adjacent band where the vapor specie of interest does not absorb. The desired special surface characteristics of the background surface is high laser radiation absorption and low thermal conductivity. These characteristics cause the surface temperature to rise very rapidly when subjected to incident laser radiation. Such materials include balsa wood and other materials that conduct only along a plane perpendicular to the background surface. One may use the specifically designed backgrounds or target boards, also known as "retroemitters" to enhance the performance of the present invention for particular applications where selection of the background is available. Another feature of the present invention that may be optionally utilized is the use of a simple receiver spectrally matched to the laser wavelength to limit back scatter to a safe level for the human eye. This receiver may be coupled to the laser to modulate the power to a safe back scatter level or shut off the laser if a safe threshold level is exceeded.

The present invention thus solves all of the aforementioned deficiencies of the prior art by providing a single wavelength, unitary laser, remote vapor detection system which is extremely sensitive and yet relatively simple in structure. Sensitivity and simplicity are obtained by the use of an absorption characteristic which is facilitated by heating the background behind the vapor or gas cloud to be detected so that the background acts as an infrared source over a broad range of wavelengths in the absorption band of interest.

OBJECTS OF THE INVENTION

It is therefore a principal object of the present invention to provide a remote vapor detection system and method thereof which is more sensitive and less complex than prior art remote vapor detection systems.

It is an additional object of the present invention to provide a remote vapor detection system and method thereof which utilizes a unitary, low power, single fixed wavelength laser as an energy source to provide a broad band absorption detection measurement process.

It is an additional object of the present invention to provide a remote vapor detection system and method thereof, which unlike the prior art does not rely on back-scatter or fluorescence or the heating of the vapor or gas cloud itself to make the detection measurement.

It is still an additional object of the present invention to provide a remote vapor detection system and method thereof which employs a single, fixed wavelength laser of relatively low power to heat the background surface behind the vapor cloud or gas cloud to be detected, the background surface, then acting as a broad band infrared source for measuring absorption characteristics of the gas or vapor specie.

BRIEF DESCRIPTION OF THE DRAWINGS

The aforementioned objects and advantages of the present invention, as well as additional objects and advantages thereof will be more fully understood hereinafter as a result of a detailed description of a preferred embodiment when taken in conjunction with the following drawings in which.

DETAILED DESCRIPTION OF A PREFERRED EMBODIMENT

Figure 1:
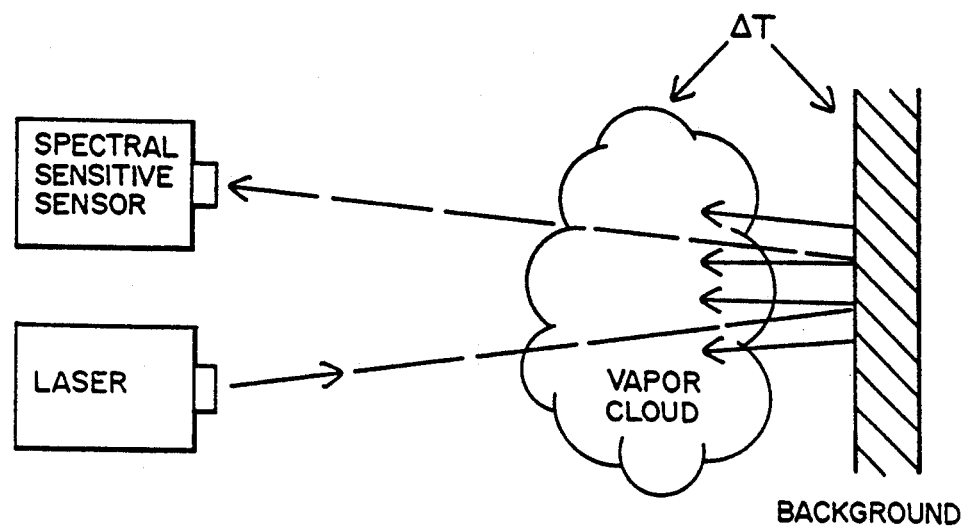
FIG. 1 is a simplified block diagram of the present invention illustrating the background heating concept thereof.
Figure 4:
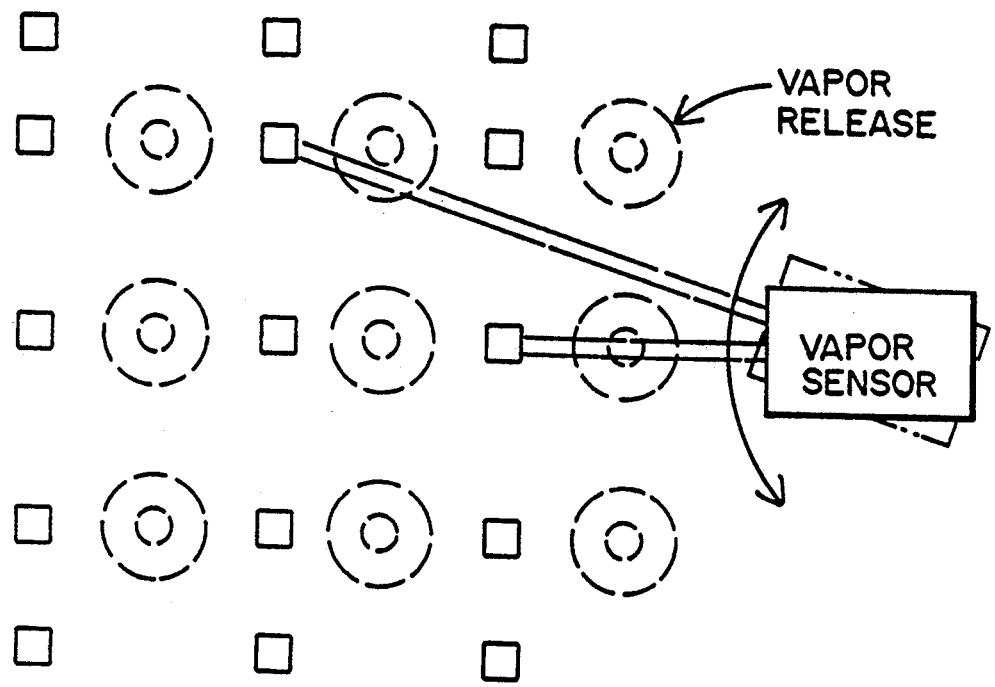
FIG. 4 is a conceptual drawing of an illustrative application of the invention using retroemitters.

The concept of the present invention may be understood best by referring to FIG. 1 in which it will be seen that a laser or other source of appropriate energy is employed to direct a beam of radiation toward a vapor cloud, at least one constituent of which is to be determined by the invention. The beam of radiation passes through the vapor cloud and irradiates the background surface behind the vapor cloud. The irradiated background surface temperature rises at a rate dependent upon the power of the incident radiation and the thermal characteristics of the background surface material. The heated background surface acts as an infrared radiator, radiating infrared energy back toward the source through the vapor cloud and over a relatively broad band such as the 8 micrometer to 12 micrometer wavelength region. As the broad band infrared radiation is transmitted by the background surface through the vapor cloud, the chemical constituents of the vapor cloud absorb energy at certain wavelengths of the infrared radiation. The characteristics of this absorbance phenomenon can thus be used to identify the content of the vapor cloud which effectively puts its absorbance fingerprint on the infrared radiation from the background surface. This absorbance fingerprint can be assessed by using for example, a spectrally sensitive sensor such as a spectrometer or radiometer with fixed filters, both of which are generically represented by a spectral sensitive sensor shown in FIG. 1. Laboratory tests have been conducted using several background materials including woods, stucco and stone and all of these tests yielded good results. However, the optimal surface characteristics of the background are high laser radiation absorption and low thermal conductivity. These characteristics cause the surface temperature of the background surface to rise very rapidly. Laboratory tests have been conducted on special materials that enhance these characteristics, such as balsa wood and materials that conduct only along a plane perpendicular to the surface area of the background. One may use these specifically designed backgrounds or target boards known as "retroemitters" to enhance the performance of the present invention in particular applications. Thus, one contemplated embodiment of the present invention includes the use of a selected background material where ever it is feasible to control the background surface. FIG. 4 illustrates one such application wherein a retroemitter is positioned behind each of a plurality of storage tanks. A source and spectrally sensitive sensor are periodically rotated through a limited angular range to point at each retroemitter for a short period. During each such period, a comparison is made between in-band and out-of-band absorption characteristics to detect any tank leakage.

Figure 2:
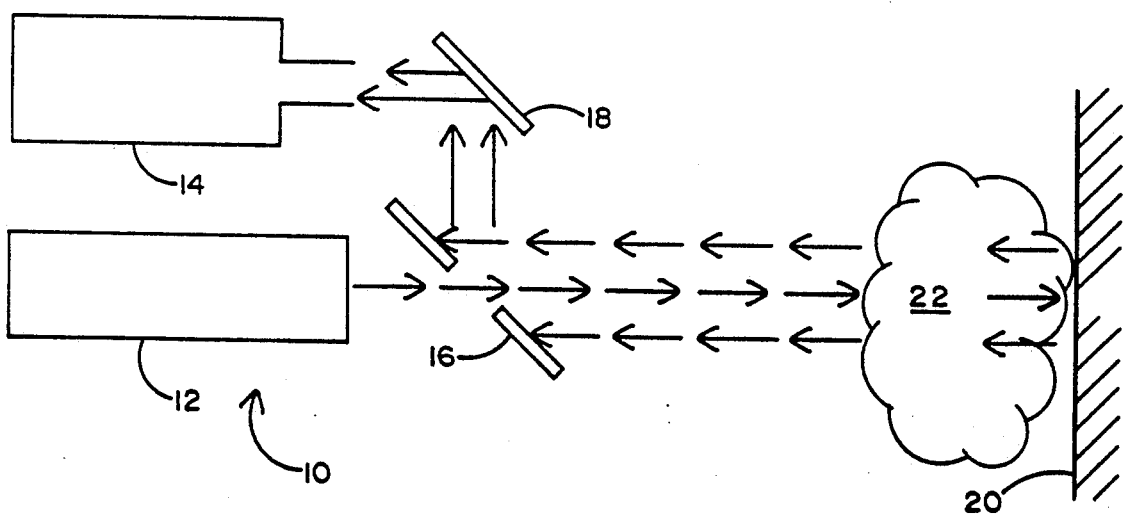
FIG. 2 is a more detailed block diagram of the present invention illustrating a mirror system used therein.

FIG. 2 illustrates a practical implementation of the concept of FIG. 1. As shown in FIG. 2, a vapor detection system 10 of the present invention comprises a laser 12, a wavelength selective receiver 14, a 45 degree oriented mirror 16 that is provided with a centrally located aperture. Mirror 16 is positioned between the laser 12 and the background surface 20 which is immediately behind and adjacent to a vapor cloud 22, the contents of which are to be detected by the present invention. A second 45 degree oriented mirror 18 is positioned adjacent the optical entrance of the infrared receiver 14. In operation, a beam from the laser 12 passes through the 45 degree mirror 16 through the vapor cloud 22 to be detected to a background surface 20. The wavelength of the laser is selected not to correspond to a strong absorption band of the vapor to be detected. Thus for example, a laser wavelength of 10.6 micrometers may be used to detect vapors such as acetone, ether, methyl ethyl ketone and freon 11. Laser energy heats the background surface 20, causing the temperature of the surface to rise. The heated background surface provides an enhanced background source of broad band infrared radiation which is then selectively absorbed by the vapor cloud 22. This broad band radiation, which has been selectively absorbed, is received by the infrared receiver 14 by means of mirror 16 and mirror 18. Receiver 14 is wavelength selective and may be in the form of a spectrometer or a radiometer with selected spectral filters. Detection occurs by measuring the infrared radiation received in a vapor absorption band and comparing it to the radiation received in an adjacent band where the vapor specie of interest does not absorb.

Figure 3:
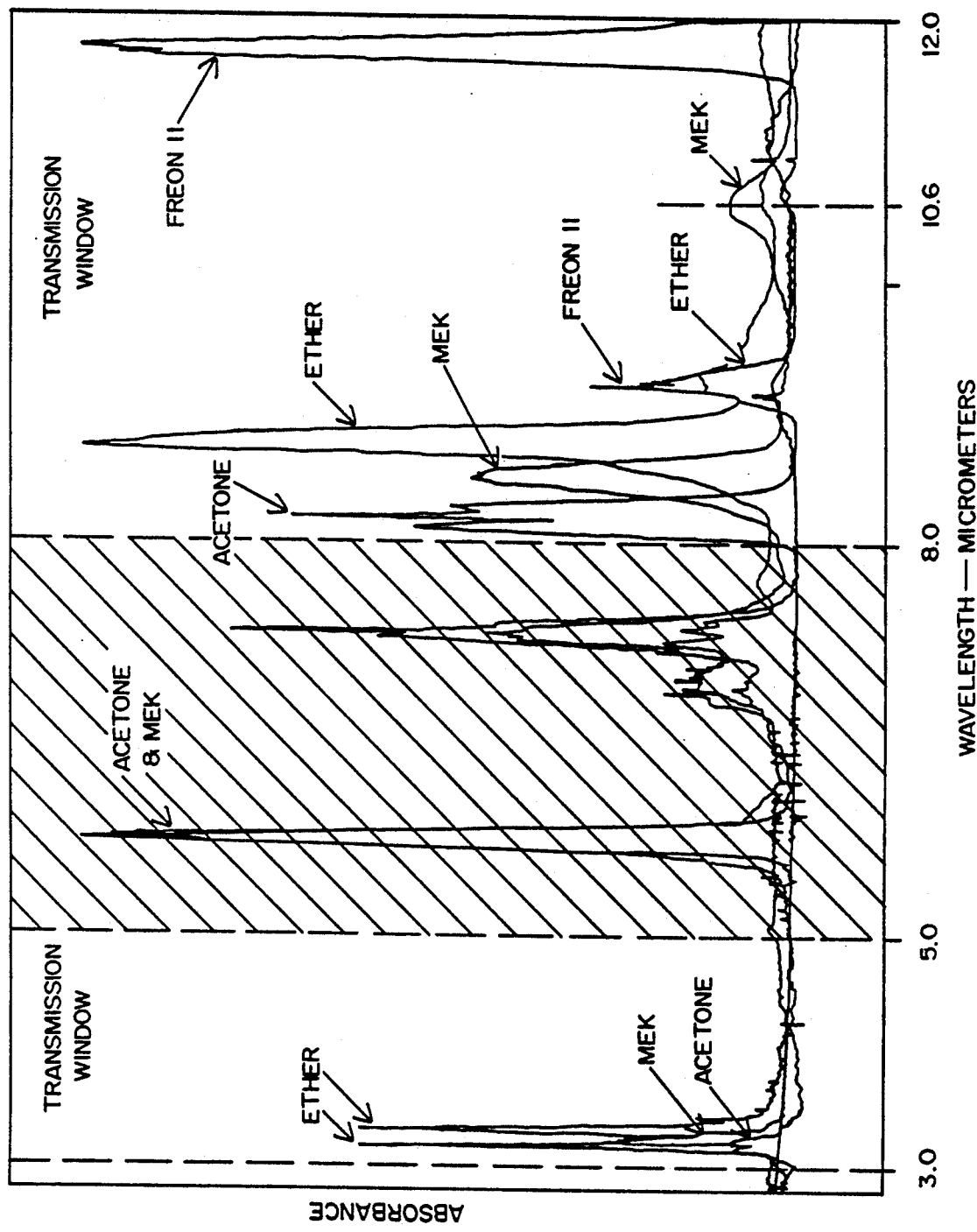
FIG. 3 is a graph of absorbance versus wavelength illustrating the absorbance characteristics of various gaseous materials in the infrared band.

This method of vapor detection may be better understood by referring to FIG. 3 which is a graph of absorbance versus wavelength for a number of common gas species of interest. The wavelength selective receiver may be a spectrometer or radiometer with filters corresponding to the absorption wavelength of the gas species of interest and at least one reference filter corresponding to a spectral region where the gas species of interest has no significant absorption. Detection is made by comparing the response of the receiver in an absorption band to the response in the reference band. In special cases where the background is not changing, an internal reference in the receiver may be used. In this special case, detection is made by measuring the temporal change in the receiver signal at the absorption wavelengths of the gas specie of interest.

In one laboratory demonstration of the present invention, an 8 to 12 micrometer receiver with an 11.6 micrometer spectral filter was placed 44½ inches from a stucco test wall, immediately in front of which was placed a vapor test cell that was used to compare the receiver response to all nitrogen versus nitrogen plus Freon 11 in a vapor test cell. A $CO_2$ laser, namely a Laakmann Electrooptic RFG series $CO_2$ laser set for 1.2 watt output, illuminated the stucco test wall at a range of 116 inches by means of a 45 degree mirror. The average receiver response was 3.28 volts for the all nitrogen gas in the test cell and 3.06 volts for nitrogen plus 2 parts-per-million concentration of Freon 11 in the nitrogen in the test cell. This is an extremely sensitive measurement since the test cell path length was only 0.5 meters which translates to a detection sensitivity of 1 part-per-million-meter which was achieved by laser heating the background stucco wall surface to approximately 70 degrees centigrade, which was approximately 45 degrees centigrade above the temperature of the vapor cloud.

It will now be understood that what has been disclosed herein comprises a novel remote vapor detection system and method thereof which advantageously utilizes only one, low power, single fixed wavelength laser to heat the background surface behind a vapor cloud, the constituents of which are to be detected. The heated background acts as a broad band infrared source for measuring absorption characteristics of the gas of vapor constituents and thus does not rely on prior art techniques such as back-scatter or fluorescence dependent measurements which inherently require greater power or suffer from reduced sensitivity. The system of the present invention comprises a source of suitable electromagnetic radiation, such as an infrared wavelength laser and a spectrally responsive receiver which may be a spectrometer or radiometer having filters at selected wavelengths corresponding to the absorption and non-absorption characteristics of the specie of gas or vapor being detected.

A preferred embodiment of the invention disclosed herein utilizes appropriate mirrors to direct the laser energy at the background surface behind the vapor cloud to be detected and then to detect the infrared energy radiated by the heated background surface in a spectrally responsive receiver. The amount of laser power required is relatively small because only a small difference in temperature between the background surface and the vapor cloud to be detected is required.

Those having skill in the art to which the present invention pertains, will now as a result of the applicants' teaching herein, perceive various modifications and additions which may be made to the invention. By way of example, other sources of electromagnetic radiation suitable for heating the background surface to a temperature above the temperature of the vapor cloud or gas to be detected may be readily utilized and may in fact be preferred in some cases, depending upon the nature of the material of which the background surface is comprised. Accordingly, all such modifications and additions are deemed to be within the scope of the invention which is to be limited only by the claims appended hereto and their equivalents.

I claim:

1. A system for remotely detecting at least one constituent of a vapor or gas located adjacent to a background surface; the system comprising:
   a laser generating a beam of energy directed to said surface for heating said surface to a temperature higher than the temperature of said vapor or gas, said higher temperature causing said surface to radiate infrared energy through said vapor or gas; and a spectrally sensitive receiver positioned for receiving said infrared energy after said infrared energy has passed through said vapor or gas, a portion of said infrared energy having been absorbed at certain wavelengths, said certain wavelengths of absorption, identifying said at least one constituent.

2. The system recited in claim 1 wherein said laser generating said beam of energy operates at a wavelength which is substantially not absorbed by said constituent.

3. The system recited in claim 1 wherein said spectrally sensitive receiver comprises a spectrometer operating at infrared wavelengths.

4. The system recited in claim 1 wherein said spectrally sensitive receiver comprises a radiometer and at least one band pass filter having a center frequency corresponding to one of said certain wavelengths.

5. The system recited in claim 1 wherein said spectrally sensitive receiver comprises a measurement frequency band and a reference frequency band for comparing energy in each said respective frequency band.

6. The system recited in claim 1 further comprising at least one mirror for directing the partially absorbed infrared energy into said spectrally sensitive receiver.

7. A method for remotely detecting at least one constituent of a vapor or gas located adjacent to a background surface; the method comprising the steps of:
 a) directing a beam of laser energy onto said background surface for heating said surface to a temperature higher than the temperature of said vapor or gas;
 b) providing a spectrally sensitive receiver in a position for receiving infrared radiation from the heated surface, said radiation having passed through said vapor or gas and having been partially absorbed by said at least one constituent at certain wavelengths indicative of said at least one constituent; and
 c) comparing radiation received from said surface at least one of said certain wavelengths to radiation received from said surface at a non-absorbed wavelength for detecting said at least one constituent.

8. The method recited in claim 7 wherein step c) is performed by providing at least one filter at one of said certain wavelengths and at least one filter at a wavelength not absorbed by said at least one constituent.

* * * * *